(12) United States Patent
Christenson et al.

(10) Patent No.: US 6,662,114 B1
(45) Date of Patent: Dec. 9, 2003

(54) METHODS FOR EVALUATING THERAPIES AND PREDICTING CLINICAL OUTCOME RELATED TO CORONARY CONDITIONS

(75) Inventors: Robert H. Christenson, Joppa, MD (US); Show-Hong Duh, Ellicott City, MD (US); Robin T. Vollmer, Durham, NC (US); E. Magnus Ohman, Durham, NC (US); Trevor D. Thompson, Lilburn, GA (US); L. Kristin Newby, Durham, NC (US); Robert M. Califf, Durham, NC (US)

(73) Assignees: Duke University, Durham, NC (US); University of Maryland, Baltimore, MD (US)

( * ) Notice: Subject to any disclaimer, the term of this patent is extended or adjusted under 35 U.S.C. 154(b) by 0 days.

(21) Appl. No.: 09/642,905

(22) Filed: Aug. 21, 2000

Related U.S. Application Data

(60) Provisional application No. 60/150,295, filed on Aug. 23, 1999.

(51) Int. Cl.[7] .......................... G01N 33/48; C12Q 1/00; C12Q 1/48; G06G 7/48
(52) U.S. Cl. ............... 702/19; 435/4; 435/15; 703/11
(58) Field of Search ............... 702/19; 435/4, 435/15; 703/11

(56) References Cited

U.S. PATENT DOCUMENTS

| | | | |
|---|---|---|---|
| 4,998,535 A | 3/1991 | Selker et al. | 128/696 |
| 5,246,001 A | 9/1993 | Ohman et al. | 128/630 |
| 5,860,917 A | 1/1999 | Comanor et al. | 600/300 |
| 6,033,364 A | 3/2000 | Ohman et al. | 600/300 |

FOREIGN PATENT DOCUMENTS

| | | |
|---|---|---|
| EP | 0887759 A1 | 12/1998 |
| WO | WO97/06725 | 2/1997 |

OTHER PUBLICATIONS

Carrier et al., Cardiac Troponin T and Creatine Kinase MB Isenzyme as Biocehmical Markers . . . , 1994, The Journal of Heart and Lung Transplantation, vol. 13, No. 4, pp. 696–700.*

Dissmann et al., Estimation of enzymatic infarct size: Direct comparison of the marker enzymes creatine kinaws and x–hydroxybutyrate dehydrogenase, 1998, American Heart Journal, vol. 135, No. 1, pp. 1–9.*

(List continued on next page.)

Primary Examiner—Ardin H. Marschel
(74) Attorney, Agent, or Firm—Myers Bigel Sibley & Sajovec

(57) ABSTRACT

A method for predicting the clinical outcome for a patient after the patient has received therapy for an acute coronary syndrome such as myocardial infarction comprises: (a) optionally, but preferably, detecting a first variable comprising a serum creatine kinase-MB release curve area in the patient after initiation of said therapy; (b) detecting a second variable comprising a serum creatine kinase-MB release curve maxima in the patient after initiation of said therapy; then (c) optionally, but preferably, detecting a third variable comprising the slope of the descending portion of the serum creatine kinase-MB release curve after initiation of said therapy (wherein a steep slope for said descending portion is a more favorable indicator of clinical outcome than a shallow slope); and (d) generating a prediction of clinical outcome for said patient from the variables collected above. The method is useful in conjunction with established therapies such as thrombolytic therapy, and is particularly useful as a surrogate end point in clinical trials of new potential therapies.

24 Claims, 1 Drawing Sheet

OTHER PUBLICATIONS

Cobb et al., *Effect of Extension of Infarction on Serial CK Activity*, Circulation 60:145–154 (1979).

Grande et al., *Estimation of Acute Myocardial Infarct Size in Man by Serum CK–MB Measurements*, Circulation 65:756–764 (1982).

Gruppo Italiano per lo Studio della Streptochinasi nell'Infarto Miocardico (GISSI), *Effectiveness of Intravenous Thrombolytic Treatment in Acute Myocardial Infarction*, Lancet 1:397–402 (1986).

Hermens et al., *Complete Recovery in Plasma of Enzymes Lost from the Heart After Permanent Coronary Artery Occlusion in the Dog*, Circulation 81:649–659 (1990).

Horder et al., *Plasma Enzymes in Myocardial Infarction. An Appraisal of Quantitative, Clinical and Pathophysiological Information*, Scand J Clin Lab Invest 41:41–47 (1981).

Jarmakani et al., *Effect of Reperfusion on Myocardial Infarct, and the Accuracy of Estimating Infarct Size from Serum Creatine Phosphokinase in the Dog*, Cardiovasc Res 10:245–253 (1976).

Norris et al., *Clinical Measurement of Myocardial Infarct Size*, Circulation 51:614–620 (1975).

Ong et al., *A Physiologically Based Model of Creatine Kinase–MB Release in Reperfusion of Acute Myocardial Infarction*, Am J Cardiol 64:11–15 (1989).

Roberts et al., *An Improved Basis for Enzymatic Estimation of Infarct Size*, Circulation 52:743–754 (1975).

Roberts, *Enzymatic Estimation of Infarct Size*, Circulation 81:707–710 (1990).

Roe et al., *A Sensitivity Analysis of Enzymatic Estimation of Infarct Size*, Circulation 52:1–5 (1975).

Roe et al., *The Relationship Between Enzymatic and Histologic Estimates of the Extent of Myocardial Infarction in Conscious Dogs with Permanent Coronary Occlusion*, Circulation 55:438–449 (1977).

Roe, *Validity of Estimating Myocardial Infarct Size from Serial Measurements of Enzyme Activity in the Serum*, Clin Chem 23:1807–1812 (1977).

Ryan et al., *The Creatine Kinase Curve Area and Peak Creatine Kinase After Acute Myocardial Infarction: Usefulness and Limitations*, Am Heart J 101:162–168 (1981).

Schwerdt et al., *Optimised Function for Determining Time to Peak Creatine Kinase and Creatine Kinase–MB as Non–invasive Reperfusion Indicators After Thrombolytic Therapy in Acute Myocardial Infarction*, Cardiovasc Res 24:328–334 (1990).

Seber et al., Nonlinear Regression. New York: John Wiley and Sons, 587–627 (1989).

Shell et al., *Early Estimation of Myocardial Damage in Conscious Dogs and Patients with Evolving Acute Myocardial Infarction*, J Clin Invest 52:2579–2590 (1973).

Shell et al., *Quantitative Assessment of the Extent of Myocardial Infarction in the Conscious Dog by Means of Analysis of Serial Changes in Serum Creatine Phosphokinase Activity*, J. Clin. Invest. 50: 2614–2625 (1971).

Sobel et al., *Estimation of Infarct Size in Man and its Relation to Prognosis*, Circulation 46: 640–648 (1972).

The GUSTO Investigators, N Engl J Med 329:673 (1993).

The TIMI Study Group, *The Thrombolysis in Myocardial Infarction (TIMI) Trial*, N Engl J Med 312:932–936 (1985).

Tiefenbrunn et al., *The Impact of Coronary Thrombolysis on Myocardial Infarction*, Fibrinolysis 3:1–15 (1989).

Vatner et al., *Effects of Coronary Artery Reperfusion on Myocardial Infarct Size Calculated from Creatine Kinase*, J Clin Invest 61:1048–1056 (1978).

Vollmer et al., *Temporal Creatine Kinase Curves in Acute Myocardial Infarction*, Am J Clin Pathol 100:293–298 (1993).

Wall et al., *Accelerated Plasminogen Activator Dose Regimens for Coronary Thrombolysis*, J Am Coll Cardiol 19:482–489 (1992).

Wilcox et al., *Trial of Tissue Plasminogen Activator for Mortality Reduction in Acute Myocardial Infarction*, Lancet 2:525–530 (1988)(ASSET).

Witteveen et al., *Quantitation of Infarct Size in Man by Means of Plasma Enzyme LevelsI*, Br Heart J 37:795–803 (1975).

Witteveen et al., *Quantitation of Enzyme Release from Infarcted Heart Muscle*, Ischemic Heart Disease, Baltimore: Williams & Wilkins, 36–42 (1970).

*Randomised Trial of Intravenous Streptokinase, Oral Aspirin, Both or Neither Among 17 187 Cases of suspected Acute Myocardial Infarction:ISIS–2*, Collaborative Group, Lancet 2:349–360 (1988).

\* cited by examiner

METHODS FOR EVALUATING THERAPIES AND PREDICTING CLINICAL OUTCOME RELATED TO CORONARY CONDITIONS

RELATED APPLICATIONS

This application claims the benefit of U.S. Provisional Application No. 60/150,295, filed Aug. 23, 1999, the disclosure of which is incorporated herein by reference in its entirety.

FIELD OF THE INVENTION

The present invention concerns methods of predicting clinical outcomes such as likelihood of mortality or death, new congestive heart failure, new pulmonary congestion or the like in a patient that has received reperfusion therapy such as thrombolytic therapy.

BACKGROUND OF THE INVENTION

Myocytes contain high intracellular concentrations of biochemical markers that are released into circulation after cell death. Using mathematical functions to model the release of these markers after myocardial infarction (MI) has been under investigation since the early 1970s (S. Witteveen et al., In: Haas J H, Hemker H C, Snellen H A, eds. Ischemic Heart Disease. Baltimore: Williams & Wilkins, 36 (1970); W. Shell et al., *J Clin. Invest.* 50: 2614 (1971); B. Sobel et al., *Circulation* 46: 640 (1972); R. Roberts et al., *Circulation* 52: 743 (1975); S. Witteveen et al., *Br Heart J* 37:795- (1975); R. Norris et al., *Circulation* 51: 614 (1975); W. Ryan et al., *Am Heart J* 101: 162 (1981); P. Grande et al., *Circulation* 65:756 (1982); L. Ong et al., *Am J Cardiol* 64:11 (1989); W. Hermens et al., *Circulation* 81:649 (1990); H. Schwerdt et al., *Cardiovasc Res* 24:328 (1990)). However, many models have been criticized, because the calculated quantity of biochemical markers released from the intracellular compartment often did not accurately relate to infarct size, commonly expressed in grams of infarcted tissue, in dogs with induced coronary occlusion (C. Roe and C. Starmer, *Circulation* 52:1 (1975); C. Roe et al., *Circulation* 55:438 (1977); C. Roe, *Clin Chem* 23:1807 (1977); Horder et al., *Scand J Clin Lab Invest* 41:41 (1981); R. Roberts, *Circulation* 81:707 (1990)). This discordance may have resulted from an incomplete understanding of the complex mechanisms governing the clearance kinetics of biochemical markers after MI. Also, the effects of infarct extension (F. Cobb et al., *Circulation* 60:145 (1979)) and reperfusion (J. Jarmakani et al., *Cardiovasc Res* 10:245 (1976); S. Vatner et al., *J Clin Invest* 61:1048 (1978)) were not accounted for in these methods. Multicompartment models have been used in an attempt to relate empirical observations with the physiological processes of marker release and clearance. Better recovery in terms of grams of infarcted tissue has been reported with use of a two-compartment model for lactate dehydrogenase and creatine kinase (CK) release in permanently occluded canine models.

Although of scientific interest physiologically, calculating the precise amount of biochemical marker released after necrosis may not reflect the primary clinical objective. Additionally, most methods use permanent occlusion models for development; these physiologically-based models may not be appropriate in the thrombolytic era, where the benefit of establishing coronary artery patency has been shown (Gruppo Italiano per lo Studio della Streptochinasi nell'Infarto Miocardico (GISSI), *Lancet* 1:397–402 (1986); R. Wilcox et al., *Lancet* 2:525 (1988)(ASSET); ISIS-2 Collaborative Group, *Lancet* 2:349 (1988); the TIMI Study Group, *N Engl J Med* 312:932 (1985); The GUSTO Investigators, *N Engl J Med* 329: 673 (1993); A. Tiefenbrunn and B. Sobel, *Fibrinolysis* 3:1 (1989)).

In view of the foregoing, there is a need for new ways to predict clinical outcome for a patient after thrombolytic therapy.

SUMMARY OF THE INVENTION

A first aspect of the present invention is a method for predicting the clinical outcome for a patient after said patient has received therapy for acute coronary syndromes such as myocardial infarction. The method comprises:

(a) optionally, but preferably, detecting a first variable comprising a serum creatine kinase-MB release curve area in said patient after initiation of therapy;

(b) optionally, but preferably, detecting a second variable comprising a serum creatine kinase-MB release curve maxima in said patient after initiation of therapy; and then (c) optionally, but preferably, detecting a third variable comprising the slope of the descending portion of the serum creatine kinase-MB release curve after initiation of therapy (wherein a steep slope for said descending portion is a more favorable indicator of clinical outcome than a shallow slope); and (d) generating a prediction of clinical outcome for said patient from the variables collected above. While the variables noted above are indicated to be optional, it will be appreciated that at least one of the first through third variables must actually be detected and used in the generating step. Preferably at least one of either the second or third variables is actually detected and used in the generating step.

The foregoing and other objects and aspects of the present invention are explained in detail below.

DETAILED DESCRIPTION OF PREFERRED EMBODIMENTS

Figure 1:
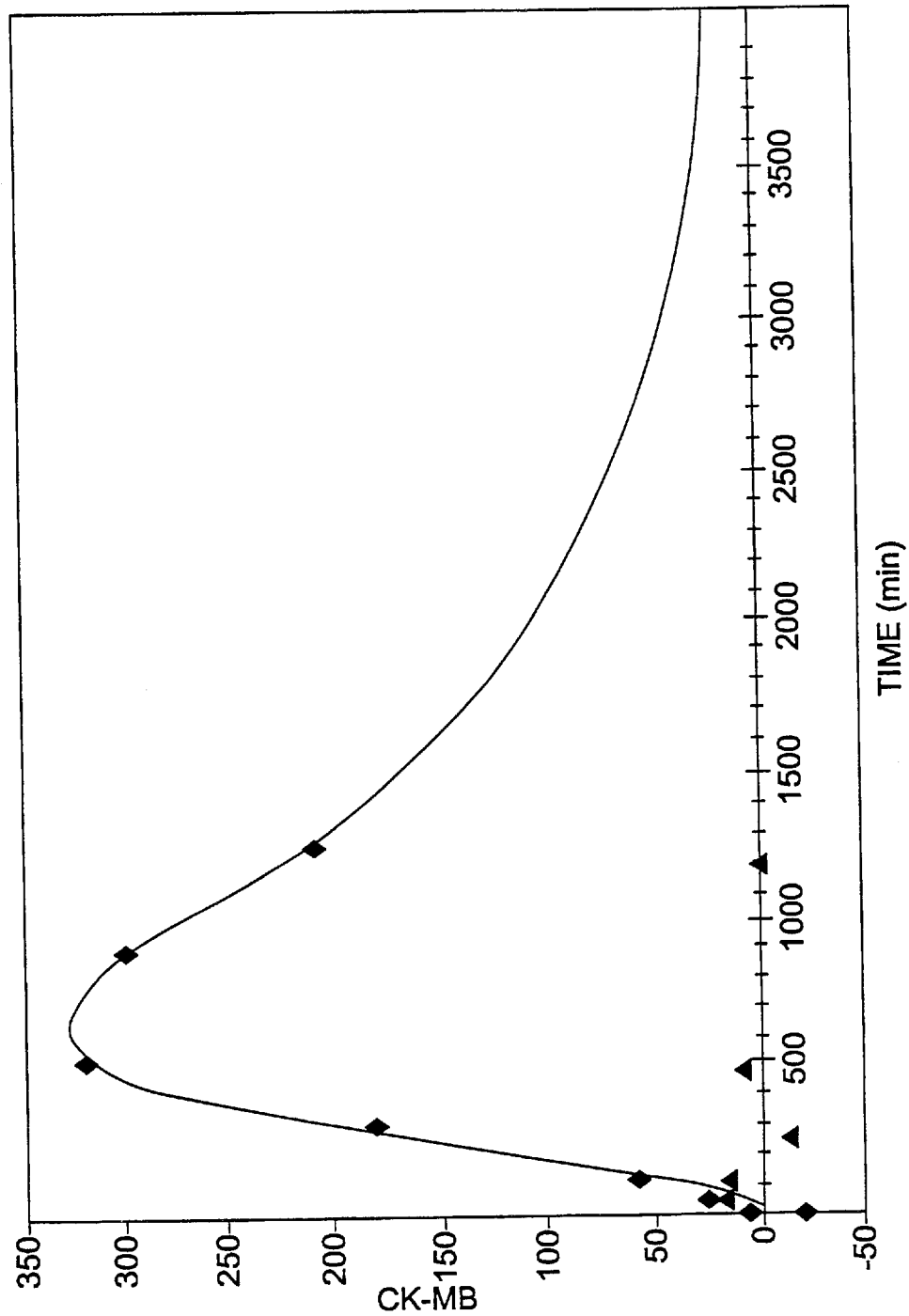
FIG. 1 illustrates a typical fitted curve with the empiric data from a patient on serum CK-MB levels in ug/L over time in minutes. Empiric data is shown as diamonds to which the curve is fitted; residuals are shown as triangles. Note the essentially random distribution of the residuals with essentially no trend over time.

The terms "reperfusion therapy" or "therapy for an acute coronary syndrome" include therapies for a range of acute coronary syndromes, including coronary ischemia with small areas of cell death, coronary ischemia with large areas of myocardial cell death, and myocardial infarct. The therapy may be a pharmaceutical or drug therapy involving the parenteral administration of an active compound to the subject, such as a thrombolytic therapy, administration of glycoprotein IIb/IIIa; the therapy may be a surgical therapy such as balloon angioplasty.

The term "thrombolytic therapy" as used herein refers to the administration of a thrombolytic compound such as a tissue plasminogen activator, a streptokinase, a urokinase, APSAC, or any other thrombolytic compound or (when the invention is used as a surrogate endpoint in a clinical trial of a potential thrombolytic agent) a potential thrombolytic compound.

A prediction of "clinical outcome" as used herein refers to a prediction (e.g., a probability or likelihood) of mortality or death, particularly cardiac death, a prediction of new congestive heart failure, a prediction of new pulmonary congestion, or the like. The prediction may be directly expressed as a likelihood of occurrence of one or more of these events, or may be indirectly expressed as a numerical value, particularly where those values are to be compiled as data in a clinical trial of a potential thrombolytic therapy.

In general, a serum creatine kinase-MB release curve is generated by collecting at least 3 or 4 to 5 or 7 serum creatine kinase-MB samples from the patient after initiation of thrombolytic therapy. For example, a "baseline" sample may be collected within ten minutes of initiation of thrombolytic therapy; and subsequent samples collected at 30 minutes, 90 minutes, 3 hours, 8 hours and 20 hours after initiation of thrombolytic therapy. The absolute time of collection is not critical, and may be about a range around the indicated times. Preferably, however, at least one of said serun creatine kinase-MB samples is collected from the patient more than three or four hours after initiation of the thrombolytic therapy.

The generating step may be carried out in accordance with known techniques, such as with an empirically-based model of actual clinical experience. The model may be updated to include the clinical experience of each patient on which it is practiced. Preferably, the model is a regression model.

Curve fitting is carried out in accordance with known techniques. In general, curve fitting should be carried out so that fit is confirmed by visual inspection; so that the number of iterations to try to achieve the fit is not greater than 50; and so that residuals show no substantial trends over time.

A particularly useful application of the present invention is in a method of evaluating the efficacy of a potential therapeutic compound (e.g., a thrombolytic compound) for an acute coronary syndrome (e.g., myocardial infarction). Such evaluations, carried out in clinical trials, typically employ actual clinical outcome as the endpoint. A surrogate endpoint, such as that provided in the instant invention, would enable the clinical trial to be conducted with fewer subjects, and/or more rapidly, and make the screening and evaluation of new potential therapeutic compounds less costly. In general, such a method comprises the steps of:

(a) administering the potential therapeutic compound to a plurality of patients (e.g., at least 50 or 100); then (b) for each of the patients, generating a prediction of clinical outcome for each of the patients in the manner described above; then (c) compiling the predictions of clinical outcomes for the plurality of patients; and then (d) determining the efficacy of the potential therapeutic compound from said compiled predictions of clinical outcomes.

Of course, efficacy need not be determined solely from the prediction provided by the method of the present invention, as the prediction of the present invention may be but one of a number of variables collected and used to determine the efficacy of the potential therapeutic compound. For example, contrast agents may be used to detect ischemic or injured tissue by imaging techniques (e.g., x-ray, ultrasound, etc.) and this data combined with the data provided by the instant invention. Thus, imaging data of the heart of the patient may serve as a fourth variable for use in the generating and/or determining step.

The present invention is explained in greater detail in the following non-limiting examples. As used herein, "CHF" means congestive heart failure; "CK-MB" means creatine kinase-MB; "PTCA" means percutaneous transluminal coronary angioplasty; "TAMI" means Thrombolysis and Angioplasty in Myocardial Infarction (trial); "ROC" means receiver-operator characteristic (curve); "TIMI" means Thrombolysis In Myocardial Infarction (trial); "min" means minutes, "h" means hours, and temperatures are given in degrees Centigrade.

EXAMPLE 1

Relation of Temporal Creatine Kinase-MB Release and Clinical Outcome After Thrombolytic Therapy In brief, in-hospital outcomes and curve-fitted creatine kinase (CK)-MB variables were examined in 130 patients undergoing thrombolytic therapy and cardiac catheterization. CK-MB maxima related to infarct location and time to therapy; curve area did not. Neither maxima nor curve area related to Thrombolysis in Myocardial Infarction (TIMI) flow grade at 90 min. Both maxima and curve area predicted outcomes of congestive heart failure (CHF) and a composite of CHF or death. After adjustment for curve area, maxima was predictive of the composite endpoint. Maxima related to time to treatment, infarct location, left ventricular function, and outcome prediction.

The major clinical objective should be to relate the data to relevant patient outcomes such as post-infarction myocardial function, morbidity, and mortality. To this end, several models for predicting release of CK and CK-MB were compared; the log-normal function resulted in the best data fit (R. Vollmer et al., Am J Clin Pathol 100:293–8 (1993)). The association between CK-MB release variables from log-normal function and clinical outcomes in patients undergoing thrombolysis were also examined in a randomized trial.

1. Methods

Population. All patients were enrolled in the Thrombolysis and Angioplasty in Myocardial Infarction (TAMI)-7 study, which examined the effects of five accelerated alteplase doses on 90-min patency in 220 patients with acute MI. The study included patients between the ages of 18 and 76 years who had symptoms of acute MI for <6 h and $\geq 1$ mV ST-segment elevation in at least two inferior leads, two precordial leads, or lead I and a VL, or ST depression in leads V1 through V4. We excluded patients with prior stroke or transient ischemic attack, a bleeding diathesis, recent surgery or trauma, uncontrolled hypertension, major comorbid conditions (such as cancer), prior bypass surgery, and prior Q-wave infarction in the same electrocardiographic distribution. Details of the five drug regimens as well as inclusion and exclusion criteria for TAMI-7 have been described in detail (T. Wall et al., J Am Coll Cardiol 19:482–9 (1992)). The TAMI-7 protocol was approved by each participating center's institutional review board.

Cardiac catheterization. Patients underwent acute angiography with left ventriculography $\geq 90$ min after the start of thrombolytic therapy (n=214, 97.3%) and 5–7 days after thrombolysis (n=174, 79.1%). All angiograms were evaluated by a blinded, independent core laboratory (University of Michigan) for Thrombolysis In Myocardial Infarction (TIMI) flow grade, left ventricular ejection fraction, regional wall motion of the infarct and noninfarct zones by the Sheehan method, and visual percent stenosis of the infarct-related artery. All 130 patients in our subpopulation underwent acute catheterization and 107 (82.3%) received a follow-up catheterization.

Specimen Collection. Blood was collected in tubes containing no anticoagulant, allowed to clot, and centrifuged at 1,000 g for 10 min. The resulting serum aliquots were frozen within 90 min and maintained at −70° C. until analysis. Blood was collected during the following time windows: "Baseline," within 10 min of thrombolytic initiation; at "30 min," between 10 and 60 min after beginning thrombolytic therapy; at "90 min," between 61 and 120 min after thrombolytic therapy; at "3 h," between 121 and 480 min after thrombolytic therapy; at "8 h," between 481 and 600 min; and at "20 h," between 601 and 1,440 min. Specimens were designated into the time windows specified above; however, the exact time of collection was recorded for all specimens and used for curve-fitting.

CK-MB Measurement. All CK-MB measurements were performed with the ICON CK-MB kit (Hybritech Inc., San Diego, Calif.) in accordance with the manufacturer's instructions. The ICON CK-MB method is a two-site immunoassay, or "mass" assay, that has a claimed detection limit of 2 μg/L; all values <2 μg/L are reported as 0 μg/L. All analyses were performed by a core laboratory (Veterans Administration Medical Center, Durham) that was unaware of the treatment or patency status of the patient.

Curve-Fitting Analysis. The log-normal function (W. Shell et al., *J Clin Invest* 52: 2579 (1973)) shown below was used to curve-fit all CK-MB data as described previously (R. Volmer et al., supra):

$$y = a * \exp[-0.5 * (\ln t - b)/c)^2]$$

Here ln t is the natural logarithm of time, a is the curve amplitude or CK-MB maxima concentration, b is the time to peak and relates to the timing of myocardial reperfusion, and c is a variable relating to curve width and indicating the duration of necrosis. The data for each patient data were fitted with a program written in C computer language (R. Volmer et al., supra). The program used a partial Newton iterative method (G. Seber and C. Wild, Nonlinear Regression. New York: John Wiley and Sons, 587–627 (1989)) to modify initial estimates of a, b, and c to improve the fit in a stepwise, controlled fashion. Patient curves were truncated when the CK-MB concentration reached 7.0 μg/L, the assay's upper reference interval (data on file with Hybritech, Inc.). The fitting process never diverged; convergence of the a, b, and c variables was achieved within 50 iterations or the data were determined to be insufficient and the patient was excluded from the study. Curves for each patient were evaluated by standard criteria that included visual inspection, convergence of the data, and evaluation of the trend of residuals with time. Typical patient curves with this strategy have been published previously (R. Vollmer et al., supra). We excluded from the study patients for whom there were an insufficient number of samples for curve-fitting analysis and those whose data showed an unsatisfactory fit.

Functional Measures and Outcomes. Clinical outcomes evaluated included in-hospital mortality and new congestive heart failure (CHF). The angiographic measures have been described above.

Statistical analysis. Baseline and angiographic characteristics of patients with serial CK-MB data were compared with those of patients without serial CK-MB data. Creatine kinase-MB maxima and CK-MB curve area were examined across selected clinical characteristics and outcomes. Continuous variables are presented as medians with 25th and 75th percentiles and discrete variables as frequencies and percentages. Statistical testing was performed using the likelihood ratio chi-square for categorical variables and the Wilcoxon rank-sum test for continuous variables. Spearman rank-order correlation coefficients were calculated to measure the association between each CK-MB curve-fitted variable and left ventricular function markers. Logistic regression models were created to determine the relations of CK-MB maxima and CK-MB curve area to CHF and the composite outcome of CHF or death. Univariate models were created to determine the unadjusted relation of each curve-fitted variable to both outcomes. A multivariate model was then used to determine the relation of each calculated variable after adjusting for the other variable. Predictors in each model were tested using the likelihood ratio chi-square test. The ability of the models to predict the outcome of interest was described using the concordance index (C-Index), which is equivalent to the area under the receiver-operator characteristic (ROC) curve. A p value of ≦0.05 was considered significant. All calculations were performed using S-Plus (version 3.4, Statistical Sciences, Inc., Seattle, Wash.) or SAS (version 6.12, SAS Institute Inc., Cary, N.C.) software.

2. Results

Of the 220 patients enrolled in TAMI-7, 14 did not have specimens collected for CK-MB analysis. Of the remaining 206, 12 (5.8%) were misclassified as having an infarction and 19 (9.2%) had had a prior MI; both of these groups were eliminated from the study. An additional 45 (21.8%) either had an insufficient number of samples for curve-fitting analyses or showed an unsatisfactory fit, including two patients who died from intracranial hemorrhage. Table 1 displays baseline characteristics for both the 130 patients included in curve-fitting analysis and the 90 TAMI-7 patients who were excluded. With the exception of time to treatment, baseline data were similar for both groups.

TABLE 1

Patient Characteristics

|  | TAMI-7 Patients Included (n = 130) | TAMI-7 Patients Excluded (n = 90) | p Value* |
|---|---|---|---|
| Age (yr) | 59 (49, 67) | 60 (50, 66) | 0.927 |
| Male sex | 100 (76.9%) | 69 (77.5%) | 0.917 |
| Time from onset of chest pain to thrombolysis (min) | 168 (120, 235) | 151 (102, 215) | 0.044 |
| Time from thrombolysis to acute angiography (min) | 142 (98, 186) | 145 (95, 206) | 0.967 |
| Infarct location |  |  |  |
| Anterior | 54 (41.9%) | 35 (39.8%) | 0.759 |
| Inferior | 75 (58.1%) | 53 (60.2%) |  |
| Acute ejection fraction (%) | 51 (43, 58) | 50 (42, 57) | 0.775 |

*p value corresponds to Wilcoxon rank-sum test for continuous variables and likelihood-ratio chi-square test for discrete variables. Values are median (25th percentile, 75th percentile) or number (%) of patients. TAMI = Thrombolysis and Angioplasty in Myocardial Infarction.

Of the 176 TAMI-7 patients who had confirmed MI and no prior MI, 130 (73.8%) had a sufficient number of data points, showed convergence of the data, had no trend of residuals with time, and had curves that were appropriate upon visual inspection. FIG. 1 displays a typical fitted curve with the empiric data and residuals. Note that the triangles show the randomly distributed residuals, with no trend over time.

Selected clinical characteristics were associated with CK-MB maxima concentration and CK-MB curve area (Table 2). Patients having an anterior MI had a significantly higher CK-MB maxima than those with an inferior MI (p=0.014); no significant relationship was seen for CK-MB curve area (p=0.345). For time to thrombolytic treatment, there was a significant difference in CK-MB maxima (p=0.002) and a trend toward significance for CK-MB curve area (p=0.077). When time to treatment was categorized as <2 h versus ≧2 h, maxima and curve area both showed significant associations (p=0.001 and 0.029, respectively). Maxima and curve area showed no significant association with TIMI flow grade assessed at 90 min.

TABLE 2

Relation of Selected Clinical Characteristics and CK-MB Variables.

|  | CK-MB maxima, μg/L | CK-MB curve area μg.min/L |
|---|---|---|
| Infarct location | | |
| Anterior (n = 54) | 350 (150, 560) | 361450 (156900, 707900) |
| Inferior (n = 75) | 225 (120, 320) | 329100 (190600, 523100) |
| p value* | 0.014 | 0.345 |
| Time to thrombolytic treatment | | |
| 0–<2 h (n = 31) | 140 (75, 310) | 269300 (99540, 370800) |
| 2–<4 h (n = 67) | 300 (160, 460) | 351300 (190600, 608200) |
| ≧4 h (n = 32) | 335 (168, 465) | 387200 (226600, 548250) |
| p value† | 0.002 | 0.077 |
| TIMI flow grade at 90 min in the infarct-related artery | | |
| 0 or 1 (n = 30) | 223 (99, 380) | 265650 (178700, 465900) |
| 2 (n= 18) | 230 (135, 400) | 441150 (269300, 639500) |
| 3 (n = 77) | 280 (150, 460) | 352100 (191100, 545400) |
| p value‡ | 0.405 | 0.221 |

Values are median (25th, 75th percentiles). *p values for testing for differences in creatine kinase (CK)-MB variables for anterior versus inferior MI patients. †p values for testing for overall differences in CK-MB variables across time to treatment. ‡p value for testing for overall differences in CK-MB variables across 90-min TIMI (Thrombolysis In Myocardial Infarction) flow grades.

Table 3 shows the association of left ventricular function and CK-MB curve-fitted variables. Both ejection fraction and infarct-zone function at the 90-min catheterization showed significant associations with CK-MB maxima and CK-MB curve area. Significant associations also were shown between CK-MB maxima and both ejection fraction and infarct-zone function at 5–7 days. For CK-MB curve area, the association with ejection fraction at 5–7 days was significant; the association with infarct-zone function showed a trend toward significance. There was no significant change in left ventricular function between the 90-min and 5–7-day studies.

TABLE 3

Relationship Between Left Ventricular Function and CK-MB Variables

|  | CK-MB maxima | | CK-MB curve area | |
|---|---|---|---|---|
|  | r* | p | r* | p |
| 90-min cardiac catheterization | | | | |
| Ejection fraction (%) | −0.369 | 0.0004 | −0.283 | 0.0076 |
| Infarct-zone function (SD/chord) | −0.241 | 0.024 | −0.236 | 0.027 |

TABLE 3-continued

Relationship Between Left Ventricular Function and CK-MB Variables

|  | CK-MB maxima | | CK-MB curve area | |
|---|---|---|---|---|
|  | r* | p | r* | p |
| 5–7-day cardiac catheterization | | | | |
| Ejection fraction (%) | −0.341 | 0.0014 | −0.236 | 0.030 |
| Infarct-zone function (SD/chord) | −0.221 | 0.042 | −0.182 | 0.096 |
| Delta (90-min minus 5–7-day) | | | | |
| Ejection fraction (%) | −0.050 | 0.694 | 0.027 | 0.833 |
| Infarct-zone function (SD/chord) | +0.043 | 0.739 | 0.111 | 0.388 |

*Spearman correlation coefficient. CK-MB = creatine kinase-MB.

Various 30-day outcomes were related to CK-MB maxima and CK-MB curve area (Table 4). Patients who died or developed CHF had higher CK-MB maxima and larger CK-MB curve areas. Patients who underwent percutaneous transluminal coronary angioplasty (PTCA) had lower values for both CK-MB maxima and curve areas, although the values were not significantly lower.

TABLE 4

Relationship Between Outcomes and CK-MB Variables

| Outcomes | CK-MB Maxima μg/L | CK-MB Curve Area μg.min/L |
|---|---|---|
| Alive (n = 124) | 240 (135, 405) | 339000 (184550, 542400) |
| Dead (n = 6) | 480 (150, 580) | 598050 (132400, 788800) |
| No congestive heart failure (n = 109) | 230 (115, 400) | 326500 (160300, 536300) |
| Congestive heart failure (n = 21) | 380 (220, 580) | 420100 (323700, 707900) |
| No rescue angioplasty (n = 109) | 260 (140, 410) | 351300 (178700, 572800) |
| Rescue angioplasty (n = 21) | 225 (99, 320) | 269400 (205300, 389500) |

Values are median, (25th, 75th percentiles). CK-MB - creatine kinase-MB.

Logistic regression modeling tested the ability of CK-MB maxima or CK-MB curve area to predict outcomes of either CHF or the composite of CHF or 30-day mortality (Table 5). In models that included CK-MB maxima or CK-MB curve area alone, both showed significant associations with an outcome of CHF. Both maxima and curve area also showed significant associations with the composite endpoint. After adjusting for CK-MB maxima, the CK-MB curve area was no longer predictive of CHF (p=0.924). Similarly, after adjustment, the CK-MB curve area did not add to the ability to predict CHF or death (p=0.617). On the other hand, CK-MB maxima remained a significant predictor of the composite of CHF or death (p=0.031) and showed a trend towards significance in predicting CHF (p=0.089). Thus, CK-MB maxima is more predictive of both CHF and the composite outcome of CHF or death.

TABLE 5

Logistic Regression Model for CK-MB
Maxima and CK-MB Curve Area

| Outcome | df | C-Index* | Unadjusted Chi-Square | p | Adjusted Chi-Square† | p |
|---|---|---|---|---|---|---|
| CHF | | | | | | |
| Maxima | 1 | 0.70 | 7.02 | 0.008 | 2.90 | 0.089 |
| Curve area | 1 | 0.657 | 4.13 | 0.042 | 0.009 | 0.924 |
| CHF or death | | | | | | |
| Maxima | 1 | 0.687 | 8.35 | 0.004 | 4.65 | 0.031 |
| Curve area | 1 | 0.645 | 3.95 | 0.047 | 0.25 | 0.617 |

*Area under the receiver-operator characteristic curve.
†Model adjusted for the other CK-MB variable.
CHF = congestive heart failure; CK-MB = creatine kinase-MB.

The previously mentioned methodology was also prospectively tested and confirmed in a set of 292 patients treated with thrombolytic therapy in acute myocardial infarction. There was a strong positive correlation between the CK-MB maxima and both the ejection fraction at 5–7 days as was previously described. More importantly, there was also a significant correlation with final infarct size as measured by sestamibi scan. These findings confirm those from the previous studies and identify CK-MB maxima and curve-fitting as a variable that can predict the amount of myocardial damage and clinical outcomes in different populations of patients receiving thrombolytic therapy.

3. Discussion

As assessed by CK-MB maxima, quantitative enzyme release increased significantly with increasing time to treatment, categorized as <2 h, 2 to <4 h, and ≧4 h, in patients receiving thrombolytic therapy. These findings are consistent with data showing that patients treated within I h of symptoms have the lowest mortality, implying that these patients have sustained less myocardial injury than patients treated later (A. Tiefenbrunn and B. Sobel, *Circulation* 85:2311 (1992)). Patients having an inferior MI showed a significantly lower CK-MB maxima than those with anterior MI. This is also to be expected because an anterior MI generally causes more extensive injury than does an inferior MI.

There was no significant relationship between TIMI flow grade at acute catheterization and either CK-MB maxima or CK-MB curve area. This may reflect that some patients who had TIMI grade 0–2 flow had PTCA performed to open the infarct-related artery. The data suggest that intervention with PTCA occurred in a time frame that served to minimize further injury, because of a difference in the CK-MB variables between patients with TIMI grade 3 flow versus grade 0–2 flow. Although there were no significant differences between the groups, patients with TIMI grade 3 flow had a generally higher CK-MB maxima. This observation probably reflects the more rapid washout characteristic of TIMI grade 3 flow, particularly since the CK-MB curve area for the TIMI grade 3 flow group was generally smaller than for the TIMI grade 2 flow group.

Left ventricular function, indicated by ejection fraction and infarct-zone function, was inversely and significantly associated with CK-MB maxima at both 90 min and 5–7 days; the CK-MB curve area showed a significant association with ejection fraction at both the 90-min and 5–7-day assessments. These data are consistent with the notion that CK-MB release is semiquantitatively related to infarct size, which in turn relates to myocardial function. Adverse outcomes, including in-hospital mortality and CHF, also were associated with higher CK-MB maxima and larger CK-MB curve areas. Patients who received rescue PTCA also had lower CK-MB maxima and smaller CK-MB curve areas.

Logistic regression was used to assess the ability of CK-MB maxima and CK-MB curve area to predict outcomes of CHF or the composite of in-hospital death and CHF. The CK-MB maxima for predicting outcome showed C-Index values, equivalent to the area under the ROC curve, in the range of 0.69, suggesting some promise for clinical use. After adjustment for curve area, CK-MB maxima significantly predicted the composite endpoint and showed a trend toward significance in predicting CHF. Curve area did not remain significant for either endpoint after adjusting for maxima. Thus, CK-MB maxima is the key variable for predicting these outcomes. In epidemiological studies comparing the likelihood of various outcomes of different treatments or interventions in patients receiving thrombolytic therapy, use of the CK-MB maxima as a surrogate may be prudent.

The log-normal function was used in this study to curve-fit CK-MB release variables after thrombolytic therapy for MI, because this equation has been shown to describe total CK-MB release (R. Vollmer et al., supra). Multicompartmental models have been favored in the past because they attempt to relate enzyme release to physiological mechanisms such as multiple tissue compartments, log-linearity of the enzyme curve, or theoretically accurate calculation of infarct size. However, we used the log-normal strategy because it fits the empirical data better than other accepted models (R. Vollmer et al., supra). The goodness-of-fit approach was used here because this strategy combines all physiological variables to yield a better overview of biochemical marker disposition. This approach is most appropriate when considering CK-MB release as one factor combined with other empirical variables such as extent of coronary disease, baseline characteristics, treatment modality, and clinical outcome.

Use of the log-normal approach in this study allowed for the objective determination of both the CK-MB maxima and CK-MB curve area. The CK-MB maxima calculated using the log-normal method consistently showed a more significant association with the variables examined than did the CK-MB curve area. This finding, in part, may reflect differences between the enzyme release pattern seen after thrombolytic therapy versus what has been more typical in the classic model of permanent occlusion (R. Roberts, supra).

There were several limitations in this study. We excluded from the analysis TAMI-7 patients who had prior MI, because the ejection fraction before enrollment would have been unpredictable. Also, although we examined the log-normal approach in a homogeneous population of patients, all of whom had ST-segment elevation and received thrombolytic therapy, about 25% of patients were not included due to an insufficient number of samples for curve-fitting analysis or unsatisfactory data fit. However, these excluded patients were similar in all baseline characteristics except time from symptom onset to thrombolytic therapy. The method did not attempt to fit curves for patients who had few CK-MB data points or whose points could not be fitted within 50 iterations. Truncation of the curve at 7.0 $\mu$g/L, the clinical cutoff for the assay used, was an objective way to prevent an artifactual increase in area caused by outliers. Another limitation was that in-hospital outcomes were used in this study. Ideally, long-term outcomes also would have been available. Finally, other methods to determine CK-MB maxima, particularly those that are less objective, may not show the same result. Further studies are needed to evaluate CK-MB maxima as a surrogate marker.

In conclusion, CK-MB maxima concentration determined from serial measurements after thrombolytic therapy showed a significant association with time to treatment, infarct location, and left ventricular function. Importantly, CK-MB maxima showed an ability to predict CHF and the combined outcome of CHF or death. Thus, this objective measurement appears to provide valuable data that are not available clinically. Combining CK-MB maxima with other variables may result in strategies that lead to further improvement. Also, this measurement may be useful for assessing improved efficacy in therapeutic trials.

The foregoing is illustrative of the present invention, and is not to be construed as limiting thereof The invention is defined by the following claims, with equivalents of the claims to be included therein.

We claim:

1. A method for predicting the clinical outcome for a patient after said patient has received therapy for an acute coronary syndrome, said method comprising the steps of:
   (a) detecting a first variable comprising an area of a serum creatine kinase-MB release curve area as a function of time in said patient after initiation of said therapy;
   (b) detecting a second variable comprising a maxima of said serum creatine kinase-MB release curve in said patient after initiation of said therapy; and then
   (c) generating a prediction of clinical outcome for said patient from said first and second variables, wherein said generating step is carried out with an empirically-based model of actual clinical experience.

2. A method according to claim 1, wherein said clinical outcome is selected from the group consisting of mortality, new congestive heart failure, and new pulmonary congestion.

3. A method according to claim 1, wherein said serum creatine kinase-MB release curve is generated by collecting at least 3 serum creatine kinase-MB samples from said patient after initiation of said therapy.

4. A method according to claim 3, wherein at least one of said serum creatine kinase-MB samples is collected from said patient more than three hours after initiation of said therapy.

5. A method according to claim 1, further comprising the step of updating said empirically-based model to include the clinical experience of said patient.

6. A method according to claim 1, wherein said generating step is carried out with a regression model.

7. A method according to claim 1, wherein said acute coronary syndrome is myocardial infarct.

8. A method according to claim 1, wherein said therapy is thrombolytic therapy.

9. A method for predicting the clinical outcome for a patient after said patient has received therapy for an acute coronary syndrome, said method comprising the steps of:
   (a) detecting a first variable comprising an area of a serum creatine kinase-MB release curve as a function of time in said patient after initiation of said therapy;
   (b) detecting a second variable comprising a maxima of said serum creatine kinase-MB release curve in said patient after initiation of said therapy; then
   (c) generating a prediction of clinical outcome for said patient from said first and second variables, wherein said generating step is carried out with an empirically-based model of actual clinical experience;
   (d) detecting a third variable comprising the slope of the descending portion of the serum creatine kinase-MB release curve after initiation of said therapy; and
   (e) generating a prediction of clinical outcome for said patient from said first, second, and third variables; wherein a steep slope for said descending portion is a more favorable indicator of clinical outcome than a shallow slope.

10. A method according to claim 9, wherein said serum creatine kinase-MB release curve is generated by collecting at least 3 serum creatine kinase-MB samples from said patient after initiation of said therapy.

11. A method according to claim 10, wherein at least one of said serum creatine kinase-MB samples is collected from said patient more than three hours after initiation of said therapy.

12. A method according to claim 9, further comprising the step of:
   detecting a fourth variable comprising imaging data of the heart of said patient after initiation of said therapy; and
   generating a prediction of clinical outcome for said patient from said first through fourth variables.

13. A method evaluating the efficacy of a potential therapeutic compound for an acute coronary syndrome, said method comprising
   (a) administering said potential therapeutic compound to a plurality of patients, and then
   (b) for each of said patients, generating a prediction of clinical outcome by:
      (i) detecting a first variable comprising an area of a serum creatine kinase-MB release curve as a function of time in said patient after initiation of said therapy;
      (ii) detecting a second variable comprising a maxima of said serum creatine kinase-MB release curve in said patient after initiation of said therapy; and then
      (iii) generating a prediction of clinical outcome for said patient from said first and second variables; then
   (c) compiling said prediction of clinical outcomes for said plurality of patients; and then
   (d) determining the efficacy of said potential therapeutic compound from said compiled predictions of clinical outcomes.

14. A method according to claim 13, wherein said clinical outcome is selected from the group consisting of mortality, new congestive heart failure, and new pulmonary congestion.

15. A method according to claim 13, wherein said serum creatine kinase-MB release curve is generated by collecting at least 3 serum creatine kinase-MB samples from said patient after initiation of said therapy.

16. A method according to claim 15, wherein at least one of said serum creatine kinase-MB samples is collected from said patient more than three hours after initiation of said therapy.

17. A method according to claim 13, wherein said generating step is carried out with an empirically-based model of actual clinical experience.

18. A method according to claim 13, wherein said generating step is carried out with a regression model.

19. A method according to claim 13, wherein said acute coronary syndrome is myocardial infarct.

20. A method according to claim 13, wherein said therapy is thrombolytic therapy.

21. A method evaluating the efficacy of a potential therapeutic compound for an acute coronary syndrome, said method comprising
   (a) administering said potential therapeutic compound to a plurality of patients, and then (b) for each of said patients, generating a prediction of clinical outcome by:
  (i) detecting a first variable comprising an area of a serum creatine kinase-MB release curve as a function of time in said patient after initiation of said therapy;
  (ii) detecting a second variable comprising a maxima of said serum creatine kinase-MB release curve in said patient after initiation of said therapy; and then
  (iii) generating a prediction of clinical outcome for said patient from said first and second variables; then
(c) compiling said prediction of clinical outcomes for said plurality of patients; and then
(d) determining the efficacy of said potential therapeutic compound from said compiled predictions of clinical outcomes;
(e) detecting a third variable comprising the slope of the descending portion of the serum creatine kinase-MB release curve after initiation of said therapy; and
(f) generating a prediction of clinical outcome for said patient from said first, second, and third variables;
  wherein a steep slope for said descending portion is a more favorable indicator of clinical outcome than a shallow slope.

22. A method according to claim 21, wherein said serum creatine kinase-MB release curve is generated by collecting at least 3 serum creatine kinase-MB samples from said patient after initiation of said therapy.

23. A method according to claim 22, wherein at least one of said serum creatine kinase-MB samples is collected from said patient more than three hours after initiation of said therapy.

24. A method according to claim 21, further comprising the step of:
  detecting a fourth variable comprising imaging data of the heart of said patient after initiation of said therapy; and
  generating a prediction of clinical outcome for said patient from said first through fourth variables.

* * * * *

UNITED STATES PATENT AND TRADEMARK OFFICE
CERTIFICATE OF CORRECTION

PATENT NO.    : 6,662,114 B1
DATED         : December 9, 2003
INVENTOR(S)   : Christenson et al.

It is certified that error appears in the above-identified patent and that said Letters Patent is hereby corrected as shown below:

<u>Column 5,</u>
Lines 25-26, should read -- y = $a * \exp[(-0.5 * (\ln t - b)/c)^2]$
Here $\ln t$ is the natural logarithm of time, $a$ is the curve --

Signed and Sealed this

First Day of June, 2004

JON W. DUDAS
*Acting Director of the United States Patent and Trademark Office*